United States Patent [19]

Morrison

[11] Patent Number: 5,417,209
[45] Date of Patent: May 23, 1995

[54] METHODS FOR DETECTING INTRAOCULAR PRESSURE-RELATED TISSUE DAMAGE IN VIVO

[75] Inventor: John C. Morrison, Portland, Oreg.

[73] Assignee: State of Oregon, acting by and through the Oregon State Board of Higher Education on behalf of the Oregon Health Sciences University, Portland, Oreg.

[21] Appl. No.: 973,043

[22] Filed: Nov. 6, 1992

[51] Int. Cl.⁶ .................................................. A61B 3/16
[52] U.S. Cl. .......................................................... 128/645
[58] Field of Search ................................. 128/645–652, 128/898

[56] References Cited

U.S. PATENT DOCUMENTS 3,246,507 4/1966 Hyde ............................................ 128/645

FOREIGN PATENT DOCUMENTS 1489766 6/1989 U.S.S.R. ................................. 128/651

*Primary Examiner*—Angela D. Sykes
*Attorney, Agent, or Firm*—Allegretti & Witcoff, Ltd.

[57] ABSTRACT

This invention relates to an animal model for human ocular disease, particularly glaucoma. The invention provides methods for determining the causes of human ocular diseases, and specifically provides methods for the anatomical, histochemical and molecular biological evaluation of the effects of elevated intraocular pressure on various tissues in mammalian eyes in vivo. The invention also provides methods for non-invasively measuring intraocular pressure and for evaluating the efficacy of treatment stategies for glaucoma involving glaucoma-relieving drugs.

7 Claims, 17 Drawing Sheets

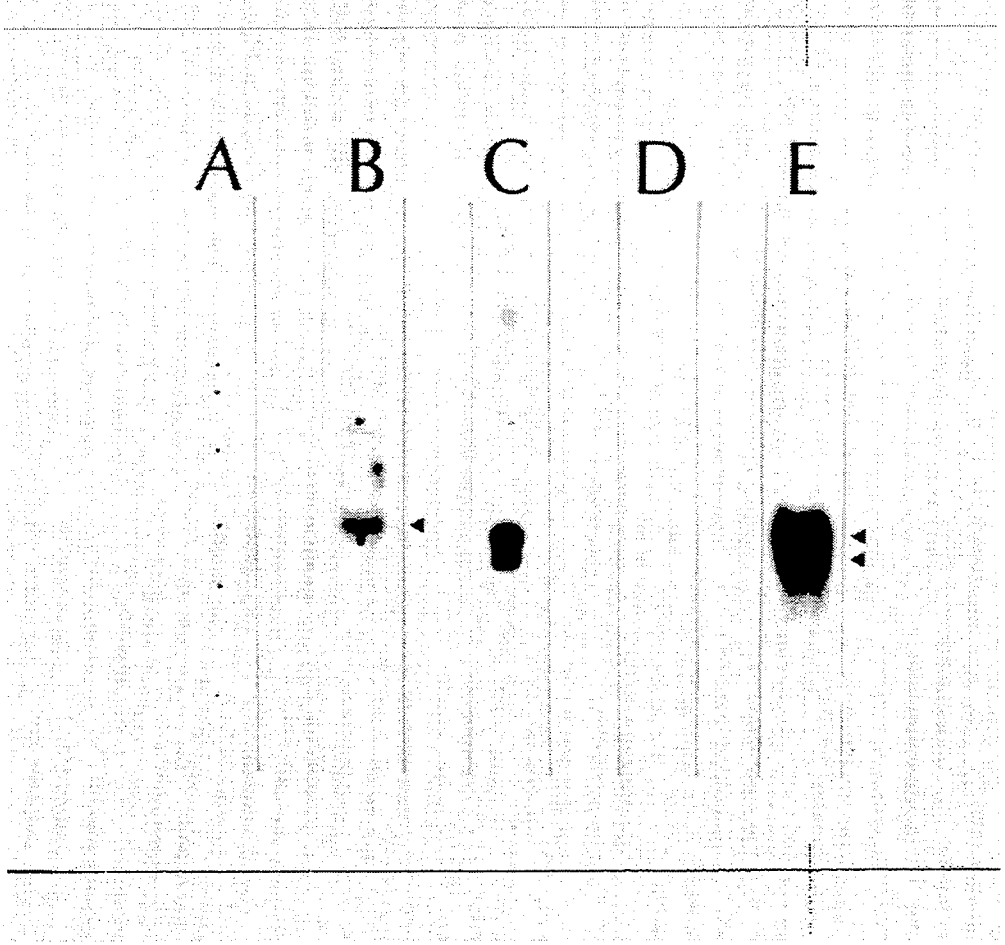

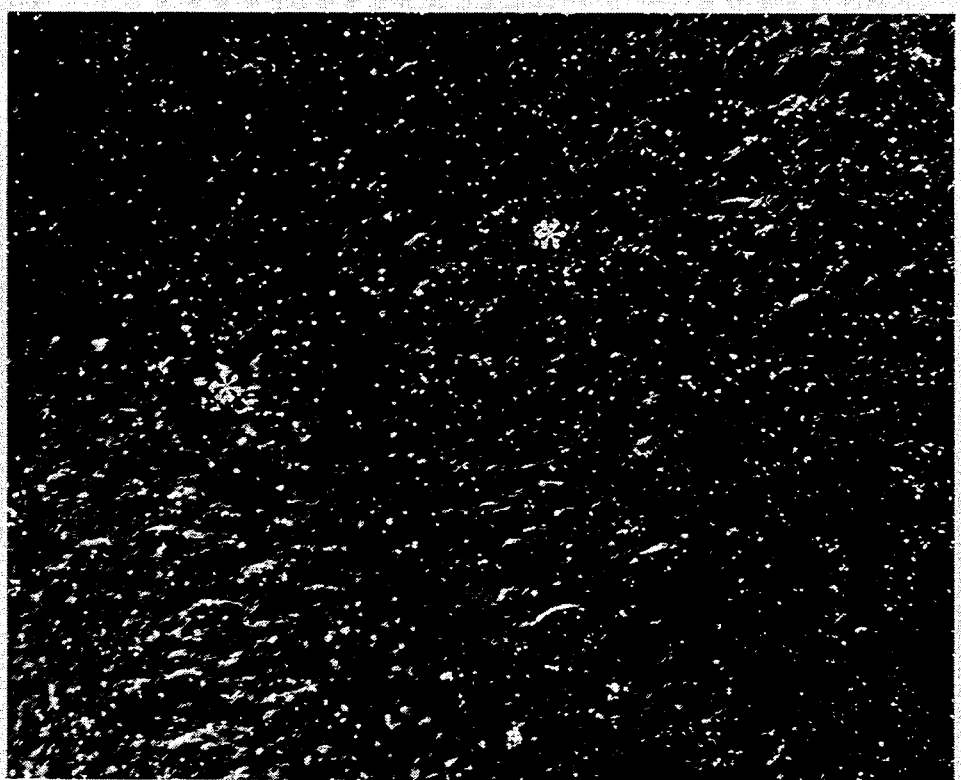

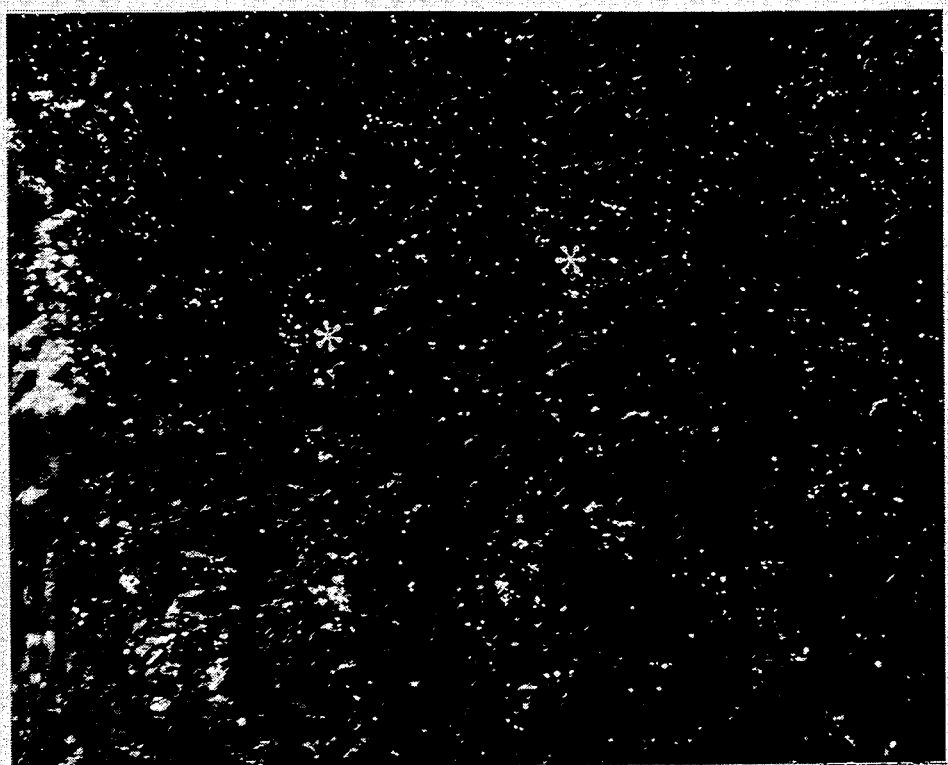

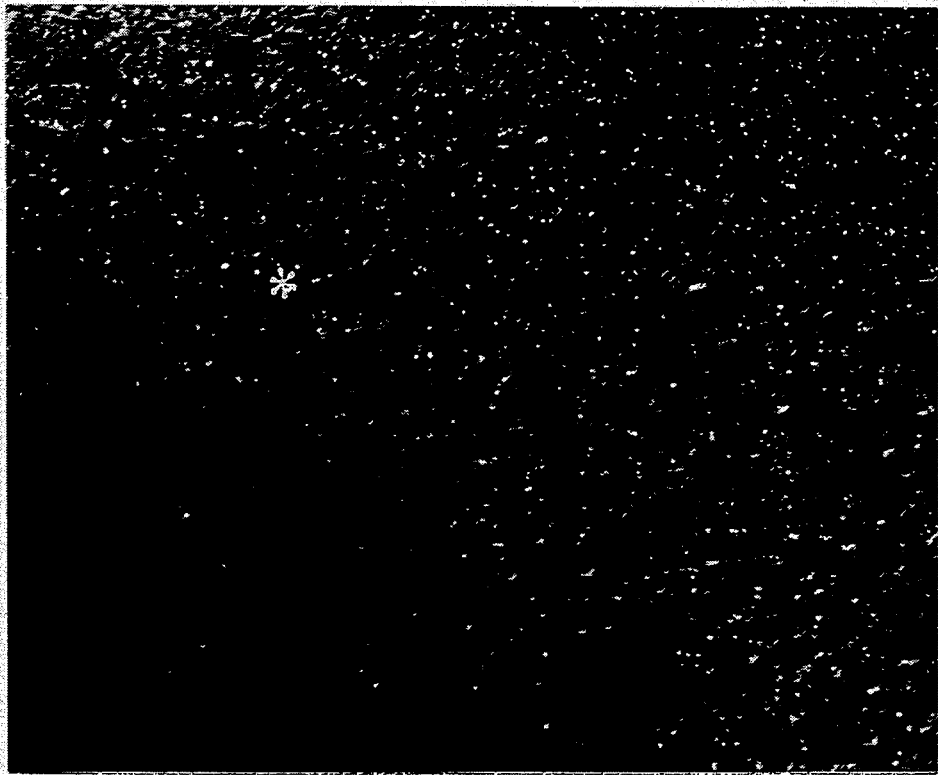

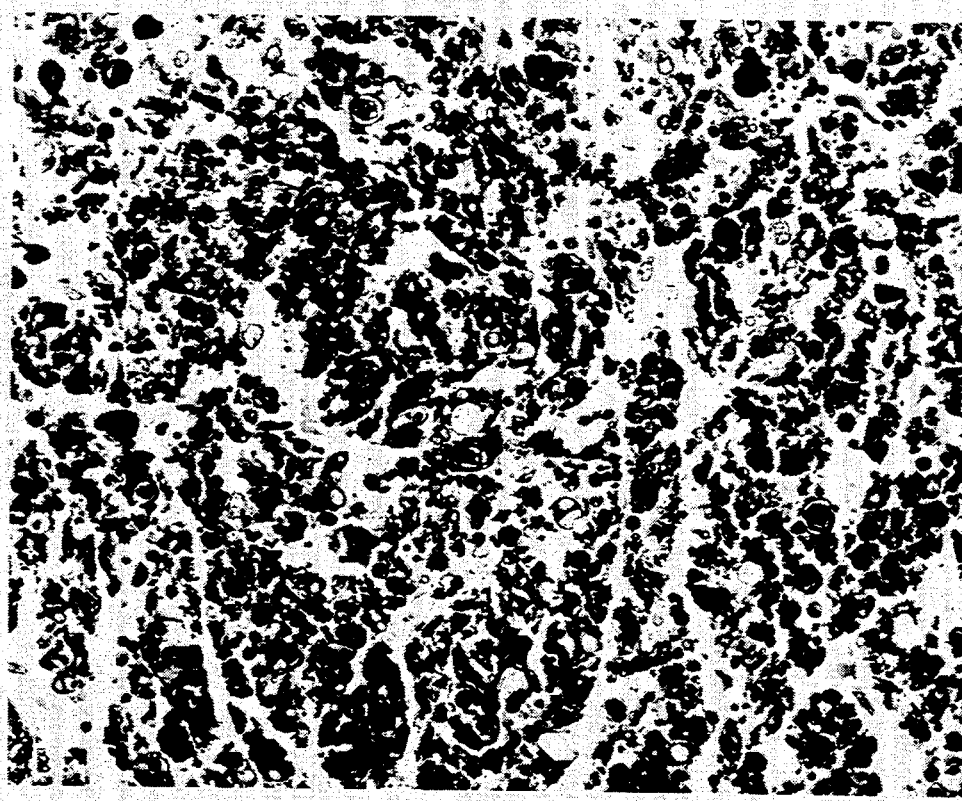
Figure IIA

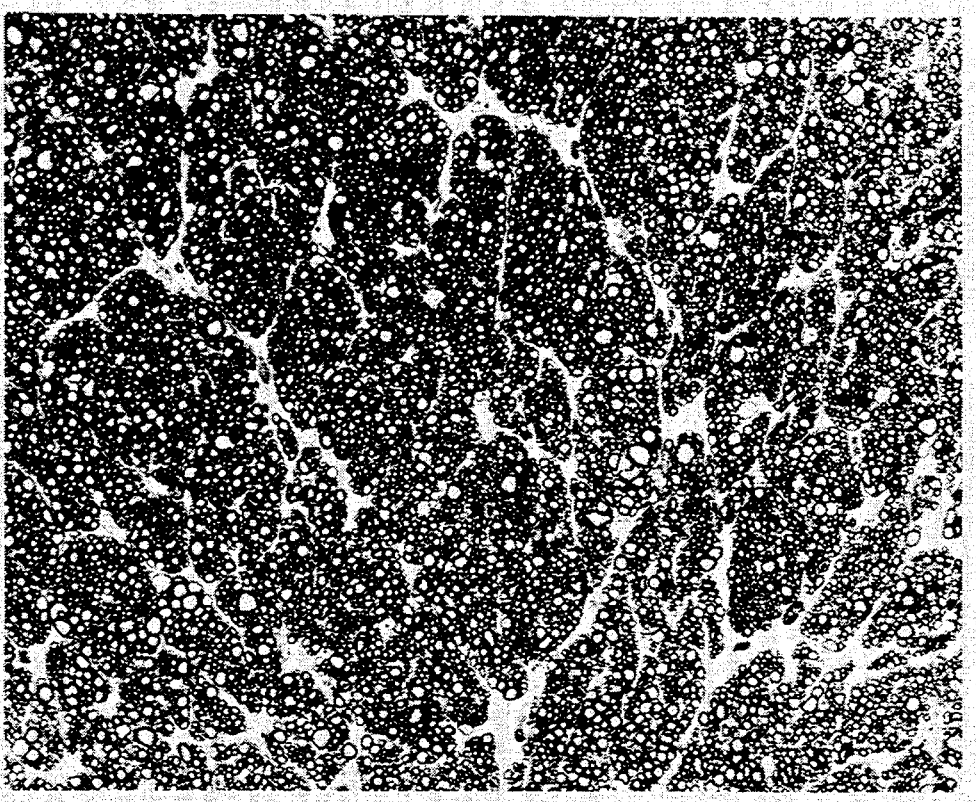
Figure IIB

METHODS FOR DETECTING INTRAOCULAR PRESSURE-RELATED TISSUE DAMAGE IN VIVO

This invention was made with government support under Grant #1-2-409-540 by the Veterans' Administration and Medical Research Foundation grant #899. The government has certain rights in the invention.

BACKGROUND OF THE INVENTION

1. Field of The Invention

The present invention relates to methods for determining the causes of human ocular diseases. In particular, the invention relates to anatomical, histochemical and molecular biological methods for evaluating the effects of elevated intraocular pressure on various tissues in mammalian eyes. The invention specifically relates to glaucoma in humans and experimentally-induced glaucoma in laboratory rats. The invention also provides methods for evaluating the efficacy of treatment strategies for glaucoma, especially those treatment strategies involving glaucoma-relieving drugs.

2. Background of the Invention

Glaucoma is a major cause of blindness, affecting nearly 2% of the adult population in the United States. In glaucoma, optic nerve fibers connecting the retina to the brain are damaged at the level of the optic nerve head, giving it a characteristic appearance termed glaucomatous optic neuropathy. Although many factors influence this process, elevated intraocular pressure (IOP; normally equal to 5-25 mm of Hg) is most well documented, and attempts to reduce elevated IOP form the basis for all current glaucoma therapy. Most instances of elevated intraocular pressure are due to increased resistance to aqueous humor outflow from the trabecular meshwork, a sieve-like ringed structure located at the juncture of the iris and cornea.

Conventional glaucoma therapy concentrates on lowering IOP either through eye drops, laser treatments, or surgery, all of which have significant drawbacks. Eye drops have been prescribed (either alone or usually in combination) either to inhibit the secretion of aqueous humor by the ciliary processes ("beta-blockers") or to improve escape of aqueous humor from the eye (miotics such as pilocarpine). To be effective, however, these drugs need to be administered in highly concentrated dosages because of poor penetration of the drugs into the eye. The administration of these drugs in such highly concentrated dosages creates a strong potential for ocular and systemic side effects, since a large percentage of the amount of these drugs administered topically to the eye(s) drain into the nose and are absorbed into the bloodstream through the nasal lining. This is particularly a problem when the drugs must be administered on a continuous basis over a patient's lifetime.

Laser treatment is often used as an alternative or in addition to drug treatment, but the results are variable and often transient. The best current surgical treatment involves creating a channel for the fluid to escape out of the eye, thereby lowering the intraocular pressure. Although effective in controlling the eye pressure, this surgery has significant potential for producing sight-threatening complications including infection and bleeding, especially immediately after surgery (when eye pressure suddenly and dramatically decreases).

All of these therapies carry risks, ranging from the systemic side effects of ocular medications to surgical complications such as abrupt, catastrophic loss of vision. Moreover, the precise benefits of lowering eye pressure in all glaucoma patients have not been unequivocally demonstrated. Furthermore, the relation of other factors to the glaucomatous process and how such factors may affect optic nerve susceptibility to IOP is poorly understood. Better understanding of these issues will provide a more rational approach to glaucoma therapy. In addition, such understanding will lead to new treatments for glaucoma that "protect" the optic nerve head in the face of elevated as well as normal intraocular pressure.

Since most forms of glaucoma are associated with elevated IOP, nearly all current glaucoma therapies are designed to lower eye pressure. Elevated IOP is the most common and best understood factor influencing the development of glaucomatous optic neuropathy (see Armaly, 1980, *Survey Ophthalmol.* 21: 139-144). In patients, elevation of IOP secondary to trauma or inflammation produces characteristic glaucomatous optic neuropathy, and nearly all humans will develop such changes if the IOP is elevated high enough on a chronic basis (Van Buskirk & Cioffi, 1992, *Am. J. Ophthalmol.* 113: 447-452). Experimental elevation of IOP in laboratory animals mimics human glaucoma, with characteristic optic nerve cupping, obstructed axoplasmic flow and preferential loss of large axons (see de Kater et al., 1986, *Invest. Ophthalmol. Vis. Sci.* 27: 1751-1754; Bunt-Milam et al., 1987, *Exp. Eye Res.* 44: 537-551; Morrison et al., 1990, *Arch. Ophthalmol.* 108: 1020-1024; Knepper et al., 1991, *Exp. Eye Res.* 52: 525-533).

However, many other factors are known or suspected to influence this process, including vascular disease, anatomy, age and prior optic nerve damage. Many patients with characteristic glaucomatous optic neuropathy do not have elevated IOP (Gliklich et al., 1989, *Ophthalmol.* 96: 316-320). This suggests that factors other than pressure may influence the glaucomatous process, or may make some individuals more susceptible to developing glaucoma, even though they have a "normal" IOP (see Cartwright et al., 1986, *Arch. Ophthalmol.* 106: 989-900). Other patients suffer from episodic vascular disturbances such as vasospasm and migraine headaches. There is some evidence that the visual field in these patients may be improved with peripheral vasodilator drugs. Although optic nerve head and retinal blood flow is efficiently autoregulated in normal animals to an IOP within 25 mm Hg of the mean arterial pressure (Drance et al., 1988, *Am. J. Ophthalmol.* 105: 35-39), non-invasive studies in normal humans suggest that autoregulation deteriorates when IOP rises above 27 mm Hg (Riva et al., 1986, *Invest. Ophthalmol. Vis. Sci.* 27: 1707-1712). Diabetes has also been associated with glaucomatous optic neuropathy. In light of these clinical observations, optic nerve head susceptibility may be linked to a defect in vascular autoregulation, either pre-existing or wherein such autoregulation deteriorates when the IOP rises above 27 mm Hg (Riva et al., ibid.).

Age and optic nerve head structure appear to be other factors involved in the development of glaucomatous optic neuropathy. Increases in susceptibility of the superior and inferior regions of the optic nerve head appear to correlate with regional variations in the structure of the lamina cribrosa, whereby the laminar beams are more sparse and thin in these regions, thereby providing less support for axon bundles (see Quigley et al., 1983, *Am. J. Ophthalmol.* 95: 673-691). Glaucomatous optic neuropathy is also more common in myopic patients whose discs are often larger than normal (Wilson et al., 1987, *Arch. Ophthalmol.* 105: 1066-1071; Tuulonen & Airaksinen, 1992, *Arch. Ophthalmol.* 110:211-213). Despite the fact that average intraocular pressures in black and white individuals is about the same, the incidence of glaucomatous optic neuropathy in blacks is nearly five times that in whites, suggesting that the optic nerve head is more susceptible to whatever etiological agent is ultimately responsible for glaucomatous damage in blacks (Sommer et al., 1991, *Arch. Ophthalmol.* 109: 1090). There is in addition a correlation between the incidence of glaucomatous optic neuropathy and a greater average optic disc size in the black population.

Prior optic nerve damage also appears to play a role in the development of glaucomatous optic neuropathy, correlating with the clinical impression that nerves already damaged by glaucoma are abnormally vulnerable to further elevations in IOP (Drance et al., ibid.). Also, because the total number of axons in the optic nerve gradually decrease with age (Morrison et al., 1990, *Invest. Ophthalomol. Vis. Sci.* 31: 1623), age frequently appears to be a contributing risk factor for development of glaucomatous optic neuropathy.

It is evident that the interrelationship of all of these factors must be thoroughly understood in order to develop a rational approach to glaucoma therapy that eliminates optic nerve damage and minimizes needless therapeutic risks and side effects.

Currently, the direct benefits of lowering IOP are poorly understood in many patients. This is primarily due to the lack of an inexpensive, well characterized animal model in which the detailed cellular responses of the optic nerve to elevated IOP can be studied. In addition to accurately representing many secondary forms of human glaucoma, such a model would provide crucial information on the cell biology of pressure-induced optic nerve damage. Better understanding of the cellular effects of elevated pressure on the optic nerve would improve understanding of the potential benefits of lowering eye pressure in glaucoma patients, regardless of the mechanism of optic tissue damage. In addition, increased knowledge about the events surrounding the development of pressure-induced optic neuropathy will better enable the study of human glaucoma and improve ways of evaluating the relative contributions of intraocular pressure and other potential disease-promoting factors.

Until now, most experimental animal models of glaucomatous optic neuropathy have monitored either the presumed initial event in optic nerve damage (i.e., obstruction of axoplasmic flow) or the chronic pathology of long term damage, such as histologic changes in optic nerve head structure. Since it is likely that cellular changes in optic nerve fibers and their associated glial tissues begin shortly after elevation of IOP (and before gross histologic evidence of damage becomes apparent) and persist throughout the disease process, sensitive indicators of optic nerve damage should be discovered by searching for and detecting these subtle cellular processes. These indicators may then be used to evaluate the importance of intraocular pressure as well as other factors in the glaucomatous process.

The use of monkeys of various species in experimentally-induced animal models of human glaucoma is known in the art.

Pasquale et al., 1992, *Opthalmol.* 99: 14-18 disclose the use of monkeys for evaluating the efficacy of mitomycin C treatment therapy following full sclerostomy to relieve experimentally-induced elevated intraocular pressure.

Jampel et al., 1991, *Arch. Ophthalmol.* 108: 430-435 relates to the efficacy of bioerodable polyanhydride discs containing 5-fluorouridine following filtration surgery on glaucomatous monkeys.

Alvarado, 1990, *Trans. Am. Ophthalmol. Soc.* 87: 489-514 disclose the use of liposome-encapsulated 5-fluoroorotate to promote post-surgical wound healing following glaucoma surgery on monkeys.

Lee et al., 1988, *Invest. Ophthalmol. Vis. Sci.* 29: 1692-1697 disclose the efficacy of bioerodable polyanhydride discs containing 5-fluorouridine following filtration surgery on glaucomatous monkeys.

Lee et al., 1985, *Curr. Eye Res.* 4: 775-781 relates to pharmacological testing of putative intraocular pressure lowering drugs in a laser-induced monkey glaucoma model.

Iwata et al., 1985, *Graefes. Arch. Clin. Exp. Ophthalomol.* 223: 184-189 disclose defects in retinal nerve fibres associated with argon laser-induced glaucoma in cynomolgus monkeys.

Pederson & Gaasterland, 1984, *Arch. Ophthalmol.* 102: 1689-1692 disclose the development of glaucoma in monkey eyes treated with light from an argon laser.

Gressell et al., 1984, *Ophthalomology* 91: 378-383 disclose the use of 5-fluorouracil to inhibit scar tissue formation at the site of glaucoma surgery performed on owl monkey eyes.

Quigley & Hohman, 1983, *Invest. Ophthalmol. Vis. Sci.* 24: 1305-1307 disclose the development of glaucoma in monkey eyes treated with light from an argon laser.

Similarly, the use of rabbits in experimentally-induced animal models of human glaucoma is known in the art.

Finger et al., 1991, *Arch. Ophthalmol.* 109: 1001-1004 disclose the use of microwave thermotherapy in the treatment of experimentally-induced glaucoma in rabbit eyes.

Lu et al., 1990, *J. Ocul. Pharmacol.* 6: 271-278 disclose the systemic and topical use of 6-hydroxyethoxy-2-benzothiazole sulfonamide to relieve elevated intraocular pressure in α-chymotrypsin-induced glaucoma in rabbit eyes.

Miller et al., 1990, *Ophthalmic Surg.* 21: 44-54 relates to the use of topical dexamethasone and β-irradiation in conjunction with fistulizing surgery to relieve experimentally-induced glaucoma in rabbit eyes.

Miller et al., 1989, *Ophthalmic Surg.* 20: 350-357 relates to a model for glaucoma fistulizing surgery in rabbits.

Bunt-Milam et at., 1987, *Exp. Eye Res.* 44: 537-551 disclose changes in optic nerve head axonal transport in rabbits having hereditary glaucoma.

Gherezghiher et al., 1986, *Exp. Eye Res.* 43: 885-894 relates to laser-induced glaucoma in rabbits as an animal model for primary human glaucoma.

Miller et al., 1985, *Trans. Ophthalmol. Soc. UK* 104: 893-897 describe a rabbit model for glaucoma fistulizing surgery.

Anderman et al., 1982, *J. Ft. Ophthalmol.* 5: 499-504 relates to the use of α-chymotrypsin-induced glaucoma in rabbit eyes for the evaluation of intraocular pressure-lowering drugs.

Rowland et al., 1981, *Curr. Eye Res.* 1: 169–173 disclose a circadian rhythm in intraocular pressure in rabbits.

Light-induce glaucoma in birds has also been studied.

Lauber, 1991, *J. Ocul. Pharmacol.* 7: 65–75 disclose the use of light-induced avian glaucoma to test the efficacy of anti-myopic drugs.

Lauber, 1987, *J. Ocul. Pharmacol.* 3: 77–100 provides a review of light-induced avian glaucoma as an animal model for primary human glaucoma.

de Kater et al., 1986, *Invest. Ophthalmol. Vis. Sci.* 27: 1751–1754 relates to the use of the Slate turkey, which suffers a hereditary eye disease leading to secondary angle closure glaucoma as an animal model for human glaucoma.

Takatsuji et al., 1986, *Invest. Ophthalmol. Vis. Sci.* 27: 396–400 relates to the use of albino mutant quails as an animal model for human glaucoma.

Lauber et al., 1985, *Can. J. Ophthalmol.* 20: 147–152 disclose the use of light-induced avian glaucoma to evaluate the intraocular pressure-lowering effects of timolol and pilocarpane.

A variety of other animals have been used to investigate the causes of glaucoma and the efficacy of putative glaucoma treatment strategies.

Yan et al., 1991, *Invest. Ophthalmol. Vis. Sci.* 32: 2515–2520 relates to the use of enucleated pig eyes in vitro for investigating the role of hydrogen peroxide insult in the development of primary open-angle glaucoma.

Baranov et al., 1991, *Vestn. Ofthalmol.* 107: 9–14 relates to the use of surgical intervention to relieve experimentally-induced glaucoma in rats.

Svee & Strosberg, 1986, *Invest. Ophthalmol. Vis. Sci.* 27: 401–405 disclose the therapeutic use and systemic side effects of ocular β-adrenergic antagonists in anesthetized dogs.

BRIEF DESCRIPTION OF THE DRAWINGS

FIG. 1 illustrates a Northern blot hybridized with: a detectably-labeled oligonucleotide specific for decorin (Lane C) and hybridized with a detectably-labeled riboprobe specific for decorin (Lane E).

FIGS. 2A–2C illustrate in situ hybridization analysis using a detectably-labeled riboprobe specific for decorin (Panel A), biglycan (Panel B) and tumor growth factor β (Panel C).

FIGS. 10A and 10B show selective loss of retinal ganglion cells (Panel A) compared to the control normal retina (Panel B) under conditions of chronically elevated intraocular pressure in rats.

FIGS. 11A and 11B show the destruction of optic nerve fibres (Panel A) compared with the control normal optic nerve (Panel B) under conditions of chronically elevated intraocular pressure in rats.

SUMMARY OF THE INVENTION

Figure 3A:
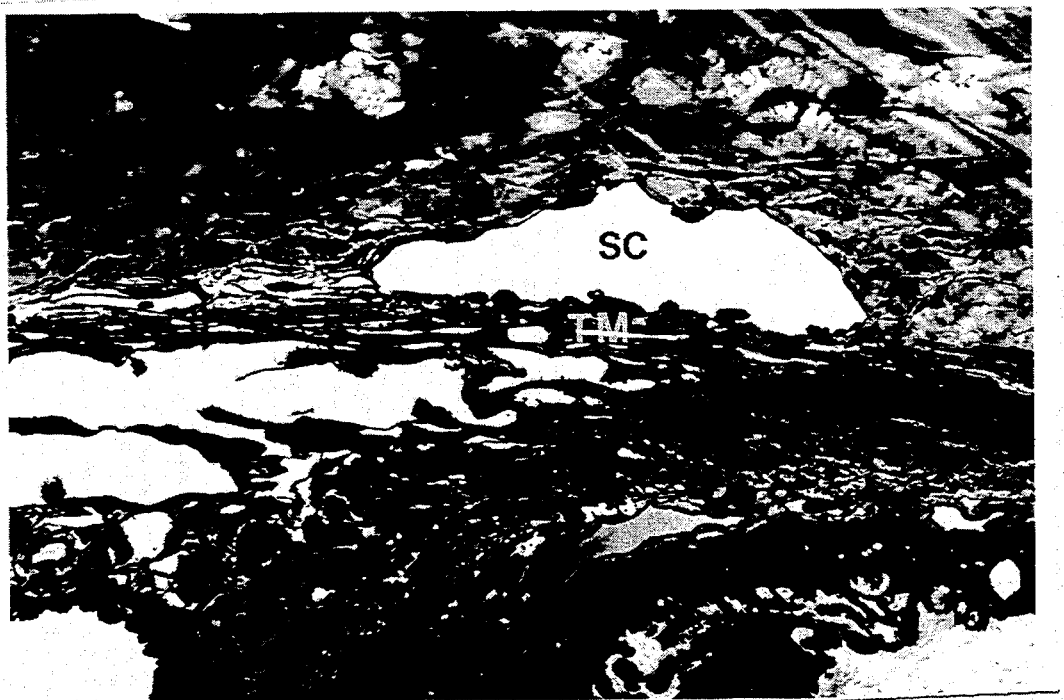
FIGS. 3A and 3B are is a histological cross-section (Panel A) and a schematic drawing (Panel B) showing the relationship of the trabecular meshwork GYM) to Schlemm's canal (SC) in the normal rat eye.

This invention provides methods for detecting optic tissue damage in vivo in response to changes in intraocular pressure (IOP).

This invention provides a unique, inexpensive, convenient animal model of pressure-induced optic neuropathy in rats. An advantage of this invention is that large numbers of animals can be studied, making it possible to apply molecular biological, biochemical and immunohistochemical techniques to uncover subtle, sensitive changes in the optic nerve and surrounding tissue structures in response to elevated IOP. In addition to the advantages of low cost and convenience, rats have long been used for neurologic research, providing a large body of scientific literature on the cell biology of neural development and injury in rats. This allows experimental results achieved using the rat model described herein to be readily integrated with information known in the art.

The invention also provides methods for evaluating the efficacy of IOP-altering drugs for the treatment of ocular diseases such as glaucoma and methods for noninvasively measuring IOP in vivo.

DETAILED DESCRIPTION OF THE PREFERRED EMBODIMENTS

1. Cellular Response to Optic Nerve Injury

Evaluation and localization of early neuronal and glial cell responses to elevated IOP is accomplished by immunohistochemical and in situ localization of selected marker proteins and their corresponding mRNAs. When neuronal tissue is injured, affected neurons and their supporting glial cells respond directly and immediately, via transsynaptic and non-synaptic communication, by activating mRNA and protein synthesis in distinctive patterns that occur in association with the simultaneous processes of degeneration and regeneration. These responses have been extensively studied in peripheral nerves, where regeneration of severed axons is usually successful, and in the mammalian central nervous system, where successful regeneration is rare. These responses have not been extensively studied in the delicate structures of the mammalian eye. These studies have, however, resulted in the identification of many neuronal and glial proteins whose rate of synthesis, concentration, or distribution are affected by the injury.

Among these proteins, several exhibit characteristics which make them useful neuronal markers for evaluating the extent of elevated IOP injury. These include T-α-1 tubulin, peripherin, growth-associated protein 43 (GAP-43), axonin-1, synaptosomal associated protein (SNAP-25) and brain derived neurotrophic factor.

Tubulin is a well-studied heterodimer consisting of two related subunits (α- and β-tubulin), accounting for 10–20% of total brain protein. Both α- and β-tubulin display a developmentally related increase in microheterogeneity in mammalian brain, some of which is generated at the transcriptional level. Of the two α-tubulin mRNAs expressed in rat brain, the T-α-1 mRNA is enriched 10 fold in embryonic compared to adult tissue and is associated with regions undergoing active neurite extension, accounting for more than 95% of total α-tubulin mRNA (see Miller et al., 1987, *J. Cell. Biol.* 105: 3065-3073). This mRNA isotype has been shown by Northern blot and in situ hybridization analysis to be rapidly induced (within 24 hrs) during nerve regeneration in the rat facial nucleus (see Miller et al., 1989, *J. Neurosci.* 9: 1452-1463). This pattern of gene expression suggests that alterations in α-tubulin expression may play a role in response to elevated intraocular pressure in the eye.

Peripherin, named for its initial discovery at the periphery of the rod outer segment disks in the mammalian eye, is a ubiquitous and exclusively neuronal intermediate filament (type III) protein, in the same family as the glial proteins vimentin and glial fibrillary acidic protein. Unlike type IV neurofilaments, whose expression is down-regulated, peripherin mRNA and protein respond to axotomy by increased expression in spinal motor neuron and large dorsal root ganglion cells, suggesting a specific structural or functional role in regenerating neurons (Wong & Oblinger, 1990, *J. Neurosci. Res.* 27: 332-341).

GAP-43 is a membrane-associated phosphoprotein which undergoes fast axonal transport and its mRNA is elevated in developing and regenerating neurons (Hoffman, 1989, *J. Neurosci.* 9: 893-897). It has also been found to be expressed in the rat retinal ganglion cells following axonal injury (Doster et al., 1991, *Neuron* 4: 635-647).

Axonin-1 is an axonal cell adhesion molecule associated with growth cones during neuronal differentiation which accumulates in the vitreous humor and cerebral spinal fluid during development (Stoeckli et al., 1991, *J. Cell Biol.* 112: 449-455).

SNAP-25 is a nerve terminal component associated with synaptogenesis. It is elevated in developing neural tissues, including retina (Catsicas et al., 1991, *Proc. Natl. Acad. Sci. USA* 88: 785-789).

Brain derived neurotrophic factor is a small basic protein structurally related to nerve growth factor, but with a central nervous system distribution and an association with cholinergic target neurons (Wetmore et al., 1990, *Exp. Neurol.* 109: 141-152); as retinal ganglion cells develop, they become dependent on the growth factor for survival.

In general, glial cell proteins are more well characterized in the art. Potential glial markers include glial fibrillary acidic protein (GFAP), vimentin, laminin B1 and tenascin.

GFAP is the predominant intermediate filament protein of mature astrocytes, and has been shown to rapidly increase in reactive gliosis, both by immunolocalization and in situ hybridization assays (McPhilemy et al., 1990, *J. Neurocytol.* 19: 494-503). In the retina, for example, Muller glial cells, which do not normally exhibit GFAP immunoreactivity, become GFAP positive throughout their cytoplasm in response to photoreceptor light damage or ischemic injury.

Vimentin, another intermediate filament protein, is normally expressed in immature glia and disappears as glia mature and express GFAP. Following axonal injury, vimentin immunoreactivity increases in both peripheral and central glia (Graeber et al., 1988, *J. Neurocytol.* 1: 3-9; Neuberger & Cornbrooks, 1989, *J. Neurocytol.* 18: 695-710). In contrast to GFAP immunoreactivity (which diffuses to nondamaged brain regions), vimentin immunoreactivity seems more specific in identifying regions of permanent, necrotic injury (Petito et al., 1990, *J. Cereb. Blood Flow & Metab.* 10: 850-859).

Laminin, a major glycoprotein component of all basal laminae, consists of α- and β-subunits. Punctate laminin deposits on glial cells precede retinal ganglion axon outgrowth along the optic nerve during embryonic development (Liesi et al., 1988, *Develop. Biol.* 130: 774-785). This punctate form of laminin has been found to be labeled by β chain antibodies only, and probably represents a variant laminin form expressed by glial cells in association with neuronal migration. At later stages, when the cells can no longer survive on a laminin substrate in vitro (but become dependent on brain derived neurotrophic factor), the laminin becomes restricted to its normal basal lamina location and labels with both α and β chain antibodies (Cohen et al., 1987, *Develop. Biol.* 122: 407-418). Transsected optic nerves become intensely laminin positive at their cut ends, where laminin is associated with axonal sprouting (Giftochristos et al., 1988, *J. Neurocytol.* 17: 385-397).

Tenascin is another glial cell adhesive glycoprotein which is abundant in embryonic tissues, including the developing retina and optic nerve and may also be a marker for glial cell activation.

2. Immunohistochemistry

Light level immunohistochemistry is performed on tissues fixed immediately after animal sacrifice. The pierced globes are fixed for up to 2 hours in 4% paraformaldehyde (depending on sensitivity of antigen to fixation), dehydrated and embedded in paraffin. 4 micron microtome sections are then cut and placed on γ-aminopropyltriethoxysilane treated slides, yielding approximately 40 sections per optic nerve head. Immunoreactivity in these sections is compared with that in fresh frozen cryostat sections.

Immunohistochemistry is performed as described (Bourne, 1983, *Handbook of Immunoperoxidase Staining Methods*, DAKO Corp.: New York). Briefly, after deparaffinization the sections are incubated for about 20 minutes in normal blocking serum, followed by incubation for 30-60 minutes in the presence of the appropriate primary antibodies, appropriately diluted in phosphate buffered saline/1% bovine serum albumen (PBS/BSA). All incubations are performed at room temperature. Following extensive washing with PBS, sections are overlayed for 30 minutes with the appropriate biotinylated secondary antibodies diluted 1:200 with PBS/BSA (Vector Laboratories, Burlingame, Calif.), and then washed with PBS and incubated for 30 minutes in avidin biotin peroxidase complex diluted 1:100 (Vector Laboratories). After washing in PBS and Tris buffered saline (TBS), sections are exposed to chromogen (0.05% 3,3-diaminobenzidine/0.02% hydrogen peroxide/TBS) for 3-6 minutes. Slides are then counterstained with hematoxylin, coverslipped and examined under both bright field and phase contrast light microscopy. Normal serum controls are used in each assay along with preabsorbed antisera.

Vimentin, also an intermediate filament protein, is considered the most specific protein for monitoring juvenile astrocytes and its immunoreactivity is lost during maturation (Dahl, 1981, *J. Neurosci. Res.* 6: 741–748). Vimentin immunoreactivity has been used to identify and study the role of retinal glia in retina neurite outgrowth in explants (Bahr, 1991, *Exp. Neurol.* 11: 65–73). In transsected peripheral nerve, vimentin becomes the predominant intermediate protein in distal Schwann cells until regeneration is complete (Neuberger & Cornbroks, ibid.). Cultured Muller cells alter their intracellular staining pattern for vimentin in response to heat shock conditions (Wakakura et al., 1989, *Exp. Eye Res.* 48: 337–350).

Commercially produced antibodies to selected glial cell markers are readily available and have been successfully used to study injury and differentiation in the rat optic system. For example, glial fibrally acidic protein (GFAP) has been extensively used as a marker for mature astrocytes and to demonstrate that Muller cells respond to injury by accumulating GFAP in a manner similar to brain astrocytes (Bignami & Dahl, 1979, *Exp. Eye Res.* 28: 63–69). Anti-GFAP antibody (Dakopatts, Copenhagen, Denmark) has been used to demonstrate increased immunostaining in transsected optic nerves (McPhilemy et al., ibid.). Monoclonal antibodies against GFAP (Clone G-A-5, Boehringer Mannheim, Indianapolis, Ind.) were used to demonstrate rapid (4–5 hr) Muller cell reactivity in peripheral retina in response to axotomy of ganglion cell axons (Seiler & Turner, 1988, *Develop. Brain Res.* 43: 111–122).

Mouse monoclonal anti-vimentin antibodies (Boehringer Mannheim), as well as polyclonal anti-GFAP antisera have been used to study the time course of maturation of that rat visual cortex (Stichel et al., 1991, *J. Neurocytol.* 20: 97–108). Monoclonal antibodies to both α- and β- chains of laminin (Upstate Biotechnology Inc., Lake Placid, N.Y.), to α-tubulin (Accurate Chemical Scientific Corp., Westbury, N.Y. and Sigma Chemical Co., St. Louis, Mo.) and to tenascin (Telios, San Diego, Calif.) are also commercially available.

3. Western blotting

Standard immunoblotting techniques are adaptable to the study of marker neuronal and glial proteins (see Harlow & Lane, 1988, *Antibodies: A Laboratory Manual*, Cold Spring Harbor: N.Y.). Briefly, brain or optic tissue samples are prepared for electrophoresis by homogenization, heating under reducing conditions and centrifugation to remove any insoluble pellet. Proteins are separated by standard SDS/PAGE electrophoresis and transferred electrophoretically to 0.2 μm nitrocellulose membranes. Proteins are visualized with 0.1% Ponceau S in 5% acetic acid (Sigma), rinsed in 5% acetic acid and then the membranes are dried several hours before immunostaining. Prestained and unstained molecular weight markers (Sigma) are used to estimate the apparent molecular weight of the protein bands. PBS-washed membrane strips are blocked one hour in 1% Carnation nonfat dried milk in PBS. Membranes are then incubated for about 2 hours with appropriately diluted primary antibodies, washed, and then incubated for about 2 hours with a 1:100 dilution of secondary antibody conjugated to alkaline phosphatase. Bands are visualized by incubation of blots so prepared with a 5-bromo-4-chloro-3-indolylphosphate/nitroblue tetrazolium substrate system (Sigma) as recommended by the manufacturer.

4. In situ hybridization

In situ hybridization is used to demonstrate and localize alterations in neuronal and glial cell marker protein mRNA synthesis in retinas and optic nerve heads from eyes having an elevated IOP. Identification of cellular sites of mRNA synthesis is particularly important for secreted protein markers, such as β-laminin and axonin-1, as well as detection of newly synthesized GFAP, which is normally abundant in mature astrocytes. The complicated structures of the retina and optic nerve head makes it essential to identify the location and type of cells responding with the synthesis of specific mRNAs. Because the change in gene expression may occur in a small number of localized cells, in situ hybridization of specific mRNAs is the methodology best suited for detecting changes in specific gene expression in these cells.

Tissues are fixed for 2 hours by immersion in 2% paraformaldehyde, then dissected and rinsed in 5× standard saline citrate buffer (SSC; 1× SSC=0.1M NaCl/0.1M Na-citrate) overnight, followed by dehydration and embedding in paraffin. Three to five micron sections are cut and laid on γ-aminopropyltriethoxysilane-treated slides.

a. Prehybridization Treatments and Hybridization

Sections are deparaffinized, rehydrated, pronase digested (if necessary) and acetylated to reduce nonspecific binding and increase probe permeability. Sections can be dehydrated and stored overnight at −70° C. Sections are then prehybridized in 3–5 mL of a solution containing standard hybridization mix (as described below for Northern blotting) plus 100 mM dithiothreitol and 500 μg/mL polyadenosine. A sufficient amount of an $^{35}$S-labeled oligonucleotide probe is then added to form a hybridization solution having a specific activity of 13 μCi/mL and incubated overnight in a waterbath at the appropriate hybridization temperature. After hybridization, the slides are briefly washed in low and high stringency wash solutions, rinsed rapidly 5 times in 0.3M ammonium acetate and dried quickly on a slide warmer.

Once dried, slides are exposed overnight to Hyperfilm Beta-Max autoradiographic film (Amersham, Arlington Heights, Ill.) to determine relative label intensity and to estimate exposure time. They are then dipped in NTB-3 (diluted 1:1 with 0.6M ammonium acetate) and stored desiccated in light-tight boxes at 4° C. for 1–3 weeks. Initially, representative groups of slides from each experiment can be developed at successive exposure times to determine the optimal time of exposure.

b. Oligonucleotide Probes

Deoxyoligonucleotide probes are used because they can be synthesized with a fraction of the effort and at a fraction of the cost of alternatives, such as recombinant DNA riboprobes or nick translation-labeled cDNA vector probes. Oligonucleotide probes are short single stranded DNA segments of defined length, thereby allowing both antisense and sense (negative control) probes to be easily obtained. They are also permeable to tissue sections. Any known base sequence can be used to efficiently design one or more probes without unnecessary delay. Oligonucleotide probes also have the advantage that they can be labeled to high specific activity.

Optimal deoxynucleotide probe sequences are comprised of between 30 and 40 basepairs in length. Such probes are determined from each marker gene sequence. Such sequences can be specifically selected in this way by scanning the EMBL database (IntelliGenetics GeneBank, Mountain View, Calif.) with numerous sequences from each marker mRNA to find potential probe sequences that have the least homology with other known sequences. Simultaneously, sense probe controls can be designed. The best sequence for each marker is then used to produce that marker's deoxyoligonucleotide antisense probe and its sense control. Marker preference is dictated by what is known about each particular marker used, both in the art and as a result of immunohistochemical results. Specificity of probes so selected are confirmed using Northern blot analysis (see below).

Oligonucleotide probes for extracellular matrix proteoglycans have been designed. The mRNA of the small proteoglycan decorin has five extended regions of base homology between bovine and human sequences. Prospective probes (38–48 bases) were checked for sequence uniqueness using the IntelliGenetics genebank databases and lack of significant base homology with abundant mRNAs such as structural proteins. Segments of the selected sequences (36–38 bases) were chosen for 50–60% guanine/cytosine content, synthesized and checked for specificity by Northern blot hybridization. Examples of Northern blot analysis in in situ hybridization utilizing the decorin oligoprobe are shown in FIG. 1 (Lane C).

c. Terminal Deoxynucleotidyltransferase Labelling

Deoxyoligonucleotide probes are radioactively labeled by the addition of a $^{35}S(\alpha\text{-thio})$ or $^{32}P$-deoxyadenosine 5' phosphate homopolymer (comprising at least 10 adenosine residues) to the probe's 3' end. This reaction is catalyzed by terminal deoxynucleotidyl transferase at room temperature with 10 pmol oligonucleotide and 135 unites enzyme in 0.5M potassium cacodylate buffer containing $CoCl_2$, 5 $\mu M$ labeled dATP and dithiothreitol (for $^{35}S$ probes).

d. Riboprobes

As an alternative embodiment, detectably-labeled probes can be syntesized by in vitro transcription of recombinant riboprobe constructs using established techniques (Promega Technical Maual: Transcription in In Vitro Systems, Promega, Madison, Wis.). For example, to obtain a biglycan riboprobe, competent JM109 bacteria were transformed with p16 biglycan plasmid DNA. The presence and orientation of the insert from the successfully isolated transformed cell clone was characterized by mini-plasmid preparation and restriction enzyme mapping. A large scale plasmid preparation was made by culturing cells from the transformed clone, lysing by the alkali method and plasmid DNA purification by precipitation with polyethylene glycol, all using standard techniques (Sambrook et al, 1989, *Molecular Cloning: A Laboratory Manual*, Cold Spring Harbor: N.Y.). Plasmid DNA was then linearized with the restriction enzyme DdeI and templates transcribed to produce radiolabeled RNA using $^{35}P$ UTP and T7 RNA polymerase. FIG. 1 (Lane E) and 2 are representative examples of Northern blot assays and in situ hybridization analysis, respectively, using riboprobes to decorin and biglycan.

5. Northern blots

A technology complementary to in situ hybridization is Northern blot analysis using neonatal or adult rat brain RNA. The use of this technique on mRNA derived from neonatal or adult rat brain tissue enables the simultaneously confirmation of probe specificity. Use of brain tissue-derived RNA for these analyses is necessary since the total number of cells responsible for synthesis of the mRNA of interest in a single retina or nerve head may be inadequate for Northern blot analysis. The alternative, pooling of tissues from several animals, is not preferred because it would require that all tissue be matched for degree and pattern of IOP rise. If necessary, Northern blot analysis can also be used to demonstrate relative amounts of specific mRNA synthesis by comparison of mRNA in pooled retina/optic nerve heads from elevated IOP and control animals. Such tissue RNA pooling techniques for Northern analysis appears to be feasible following the teachings known in this art (see Sarthy & Fu, 1990, *J. Cell Biol.* 110: 2099–2108; McPhilemy et al., ibid.).

The acid guanidinium-phenol-chloroform method of Chomczynski & Sacchi (1987, *Anal. Biochem.* 162: 157–159) is used to isolate RNA from brain and from pooled optic nerves, retinas or optic nerve heads. Immediately after removal from the animal, the tissue is minced on ice. This method utilizes a single extraction followed by isopropanol precipitation, reprecipitation with a guanidinium mixture and isopropanol, wash with ethanol and resuspension in sodium dodecyl sulfate (SDS). Such preparations reliably produce pure and undegraded RNA which can be used directly for electrophoresis and Northern hybridization, or further purified to poly(A) + RNA utilizing oligo(dT) chromatography. Yield of total RNA by this method is 0.5–2.5 $\mu g/mg$ tissue, depending on the source.

Removal of ribosomal RNAs and transfer RNA by poly(A)+ RNA preparation eliminates many of the sources of nonspecific binding in RNA preparations and improves the ability to detect low levels of specific mRNAs. A modification of the standard poly(A)+ RNA procedure was used herein (Sambrook et al., ibid.), in which 1 mg total RNA is mixed gently for 90 min at room temperature with 75 mg of oligo(dT) resin. The resulting resin/RNA mixture is poured into a RNAase free disposable column, rinsed with several volumes of high salt buffer [HSB =0.5M NaCl, 20 mM Tris buffer (pH 7.5), 1 mM disodium ethylenediaminetetractate and 0.1% SDS], followed by several volumes of intermediate salt buffer (same as HSB, except 0.1M NaCl). Finally, poly(A)+ RNA is eluted with low salt buffer (same as HSB, but without NaCl). Using this preparation, we generally obtain a yield of 1–2% of the original RNA. Poly(A)+ RNA purification may be necessary prior to electrophoresis and Northern blot analysis for less abundant marker messengers.

Purified RNA and poly(A)+ samples are separated by formaldehyde agarose gel electrophoresis and blotted by capillary transfer to Nytran TM membranes (Biorad, Richmond, Calif.) followed by immobilization by ultraviolet crosslinking. These membranes can be probed several times with different probes.

Membranes are prehybridized in sealed plastic bags in a buffered solution containing 20–60% formamide, 4× SSC and blocking compounds such as 5× Denhardts reagent (0.2% polyvinylpyrrolidone, 0.2% Ficoll, 0.2%

BSA), 200 μg/mL sheared salmon sperm DNA, and 100 μg/mL transfer RNA. The $^{32}$P-labeled probe hybridization solution (at a specific activity of approximately 1 μCi/mL) is then added and the membranes are hybridized overnight at a temperature determined by the melting temperature for the polynucleotide duplex. The membranes are then washed briefly (3–15 minutes) in low and high stringency salt solution to remove non-specifically bound probes. Wash conditions are much briefer and less temperature-dependent for oligonucleotide probes then for cDNA and riboprobes. After washing, plastic wrapped membranes are autoradiographed by exposure to preflashed Kodak XAR-2 X-ray film at −70° C. with intensifying screens.

The following Examples illustrate certain aspects of the above-described method and advantageous results. The following examples are shown by way of illustration and not by way of limitation.

EXAMPLE 1

Figure 3B:
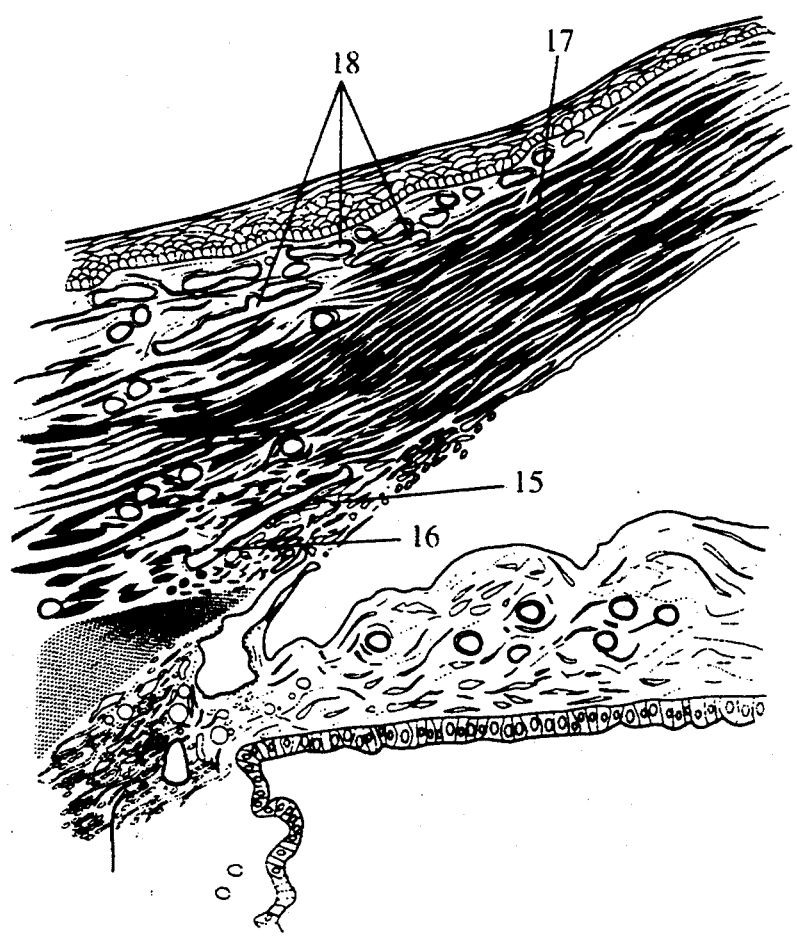

Initial attempts to produce sustained elevation of intraocular pressure in rat eyes ranged from intracameral injections of ghost red blood cells and microspheres to direct microsurgical manipulation of the anterior chamber angle in an attempt to produce permanent scarring. These efforts all met with limited success. Since it was known that the rat aqueous humow outflow system possesses a sparse, but well-defined trabecular meshwork (TM) lined by endothelial cells and a circumferential Schlemm's canal (SC) lined by endothelial cells with giant vacuoles (as shown in FIG. 3) (Tripathi & Tripathi, 1972, *Exp. Eye Res.* 14: 73–79; Van der Zyoen, 1977, *Ophthalologica* (Basel) 714: 285–298), the approach described herein had the goal of injecting sclerosing agents with which to scar the aqueous humor outflow pathways of the rat eye.

Figure 4:
FIG. 4 represents a methacrylate cast of the trabecular meshwork and Schlemm's canal (SC) from the normal rat eye.
Figure 5:
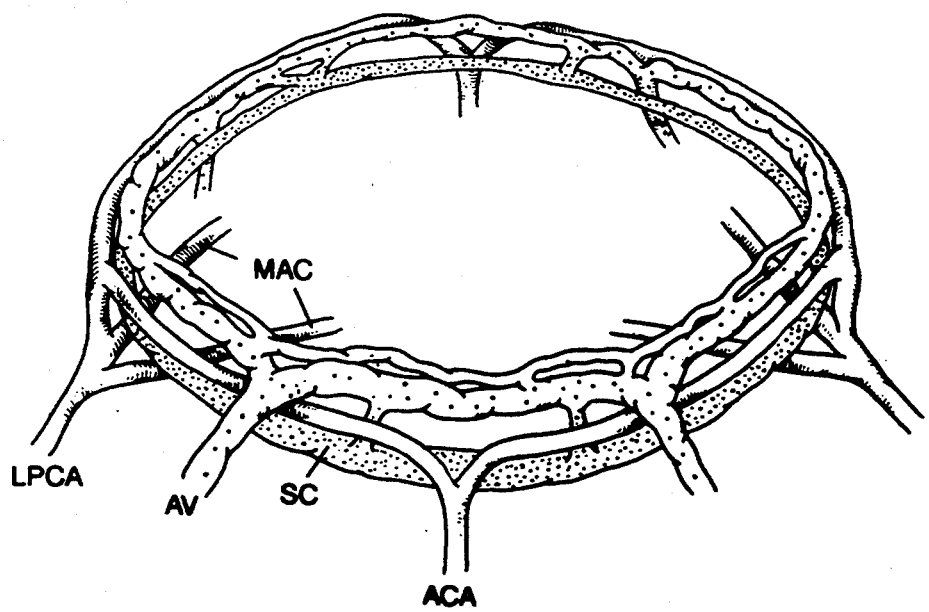
FIG. 5 is a schematic diagram illustrating the relationship between the trabecular meshwork, Schlemm's canal and the ocular vasculature in the normal rat eye.
Figure 6:
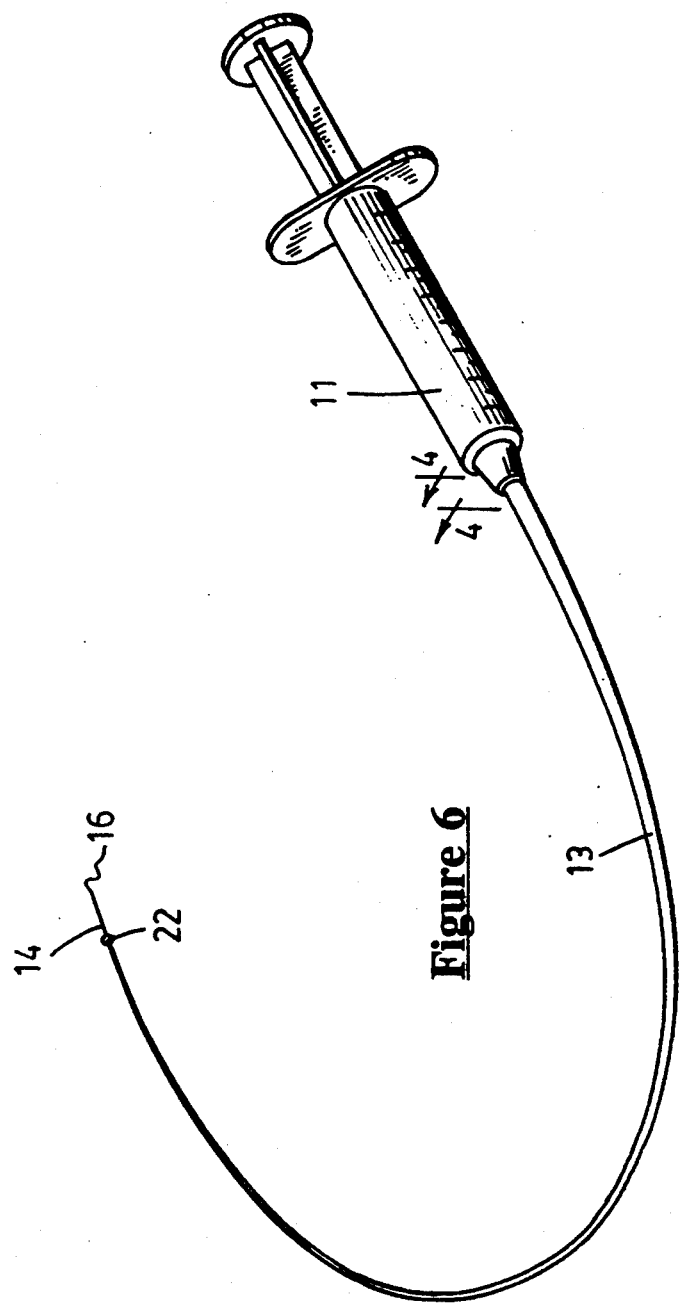
FIG. 6 is a schematic diagram of a microneedle for injecting compounds into the ocular vasculature.

This approach required the identification of the aqueous outflow veins on the surface of the rat eye. In order to identify these vessels, the anterior chamber of the eye was injected with flourescin dye, which rapidly escaped into the perilimbal vascular plexus, ultimately draining into aqueous veins in the conjectiva and episclera. Next, methylmethacrylate microvascular castings of these vessels were produced by injecting a diluted, modified Batson's methylmethacrylate casting medium into the abdominal aorta as described (Fahrenback et al., 1988, *J. Electron Microscop. Techn.* 10: 15–26), allowing the plastic to polymerize and then enucleating the eyes. After corrosion of the surrounding tissues with 6M KOH, the castings were air dried, sputter-coated with gold palladium and examined using an AMR 1000 scanning electron microscope. A representative example of such a methacrylate cast is shown in FIG. 4. A dense plexus of veins oriented circumferentially around the limbus was identified. These results also confirmed that this plexus was directly connected with a complete Schlemm's canal (SC) via numerous collector channels (identified in the Figure by as asterisk), much like the arrangement of the primate eye. These findings and the relation of these structure to the aqueous veins (AV), anterior ciliary arteries (ACA), long posterior ciliary arteries (LPCA), and major arterial circle (MAC) are diagrammed in FIG. 6.

These results revealed a pathway by which sclerosing agents could be injected retrograde into the aqueous humor outflow system of the rat eye. A minimally invasive injection of the appropriate strength solution could theoretically cause selective scarring of the trabecular meshwork and Schlemm's canal, thereby increasing the resistance to aqueous humor outflow and elevating intraocular pressure.

EXAMPLE 2

In order to inject aqueous outflow veins, a unique microneedle (shown in FIG. 6) was developed that is fine enough to cannulate the delicate episcleral veins but capable of delivering fluid at an adequate rate, disclosed more fully in U.S. patent application Ser. No. 07/866,561, hereby incorporated by reference. Briefly, a glass micropipette is heated over a bunsen burner and drawn to a fine caliber, preserving its patency. A 3 mm segment of appropriate sized needle (approximately 50 microns wide) is inserted into the small end of a tapered length of PE-50 polyethylene tubing and secured with a drop of epoxy glue. The large end of the polyethylene tubing is glued over a 23 gauge needle stub connected to a 1 cc syringe. In spite of its caliber, the short length of this needle makes it possible to inject approximately 0.1 mL of fluid over 30 seconds. This is a significant rate, considering the volume of the normal human anterior chamber is 0.25 mL. Cannulation success of small vessels is improved by beveling the needles on a diamond-dusted grinding wheel rotated at high speed on a Dremel tool.

EXAMPLE 3

Figure 7:
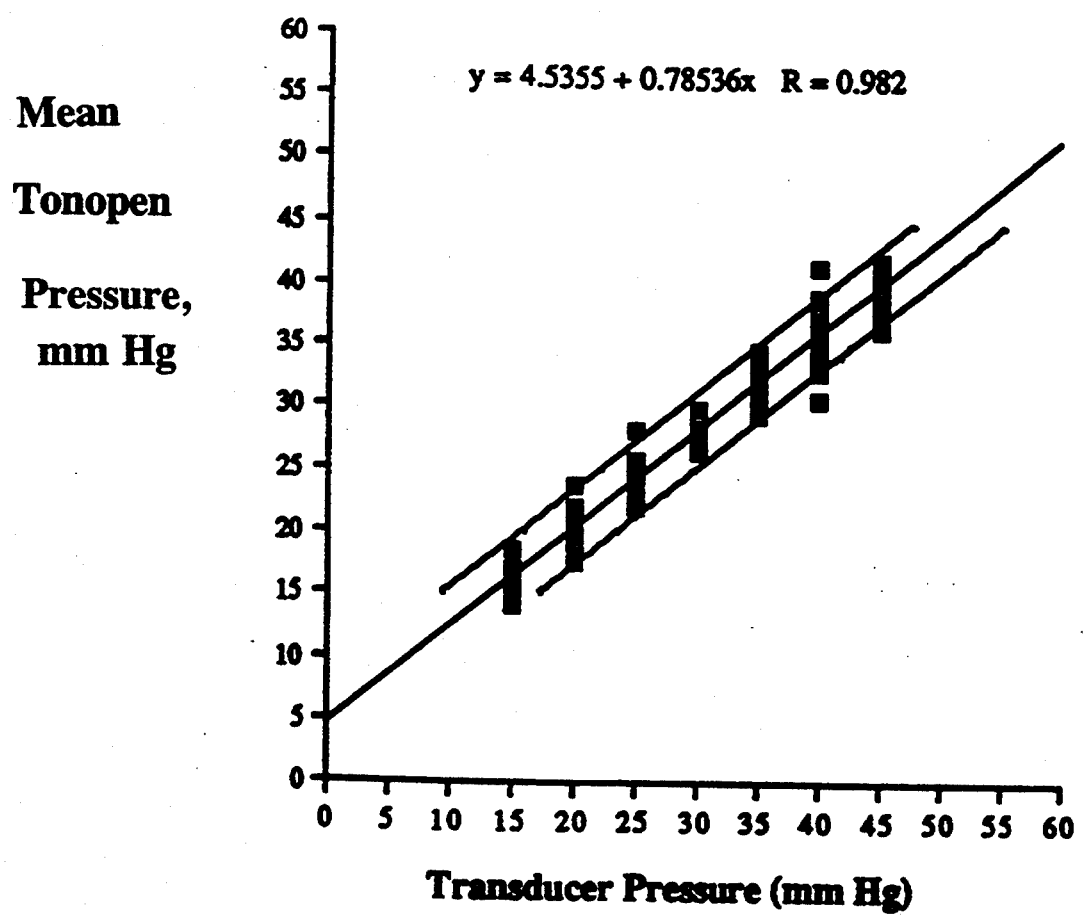
FIG. 7 is a plot of the 95% confidence interval relating actual intraocular pressure to the intraocular pressure as measured with the Tonopen 2 tonometer in rat eyes.

The feasibility of using the Tonopen 2 tonometer was evaluated as a means for non-invasive measurement of rat intraocular pressure. To accomplish this, one eye of each member of a group of 20 Brown Norway rats was cannulated with a 23 gauge needle connected simultaneously to a 1 cc syringe for varying intraocular pressure and a pressure transducer chart recorder for continuous IOP monitoring. We then obtained 15 consecutive valid Tonopen readings at pressure levels ranging in 5 mm Hg increments from 15 mm Hg to 45 mm Hg. Plotting the mean intraocular pressure at each level against actual, transducer IOP produced a graph with a straight line linear regression formula of $y=4.54+0.79\times(r=0.98)$. To test the tonopen's ability to measure unknown IOPs, a second group of 20 animals were cannulated in similar fashion and random IOP's measured with the Tonopen 2 in masked fashion. Mean Group 2 tonopen values plotted against transducer IOP yielded a regression formula of $y=4.75+0.78\times(r=0.94)$. Using 2-way analysis of variance, it was determined that the Group 2 data did not differ significantly from the Group I data. A correction factor with 95% prediction intervals for tonopen readings was generated and plotted (FIG. 7). These data indicate both the reliability and repeatability of the Tonopen 2tonometer when used on the anesthetized rat eye. Our experience also suggests that similar results may be obtained when this instrument is used in awake animals anesthetized only with topical proparacaine. Successful use of the tonopen in rat eyes requires experience and skill in recognizing valid IOP readings. This skill is best attained and maintained by frequent testing against a known pressure level, as performed in the transducer experiments described above.

EXAMPLE 4

Aqueous Vein Injections

Brown Norway rats are anesthetized with a 1.0 mL/kg intraperitoneal injection of a solution containing 5.0 mL ketamine (100 mg/mL), 2.5 mL xylazine (20 mg/mL), 1.0 mL acepromazine (10 mg/mL), and 1.5 mL sterile water. A radial aqueous vein usually branching in both directions at the superior limbus is identifiable in nearly all eyes. All other aqueous veins are temporarily occluded by a specially designed plastic clip encircling the globe at the equator to contain the injected fluid at the limbus. The eye is then rotated down and the overlying conjunctiva and connective tissue are incised and cleared from the vein. Once the vein's wall is exposed (about 3 mm length), a microneedle attached to a 1.0 cc syringe filled with 2M hypertonic saline is introduced into the field.

By carefully orienting the needle shaft directly over and parallel to the vessel with the bevel up, the needle is inserted into the vessel lumen, using a minute movement, while stabilizing the proximal portion of the vessel with straight jeweler's forceps. Because of the small vessel size, a high-power Wild dissecting microscope is used, equipped with foot-driven focus and 20× oculars to increase total magnification to 40–60×. The needle is held at the glue joint with a specially modified, curved reverse action jeweler's forceps to minimize tremor and optimize needle orientation.

Approximately 10 μL of 2M hypertonic saline can be injected over a few seconds. Injections of up to 100 μL also produce elevated IOP, but are associated with excessive anterior chamber inflammation. After the injection is completed, the eye is irrigated with balanced salt solution and topical antibiotics are instilled. The rats are allowed to recover and appear to have little postoperative discomfort.

Figure 8:
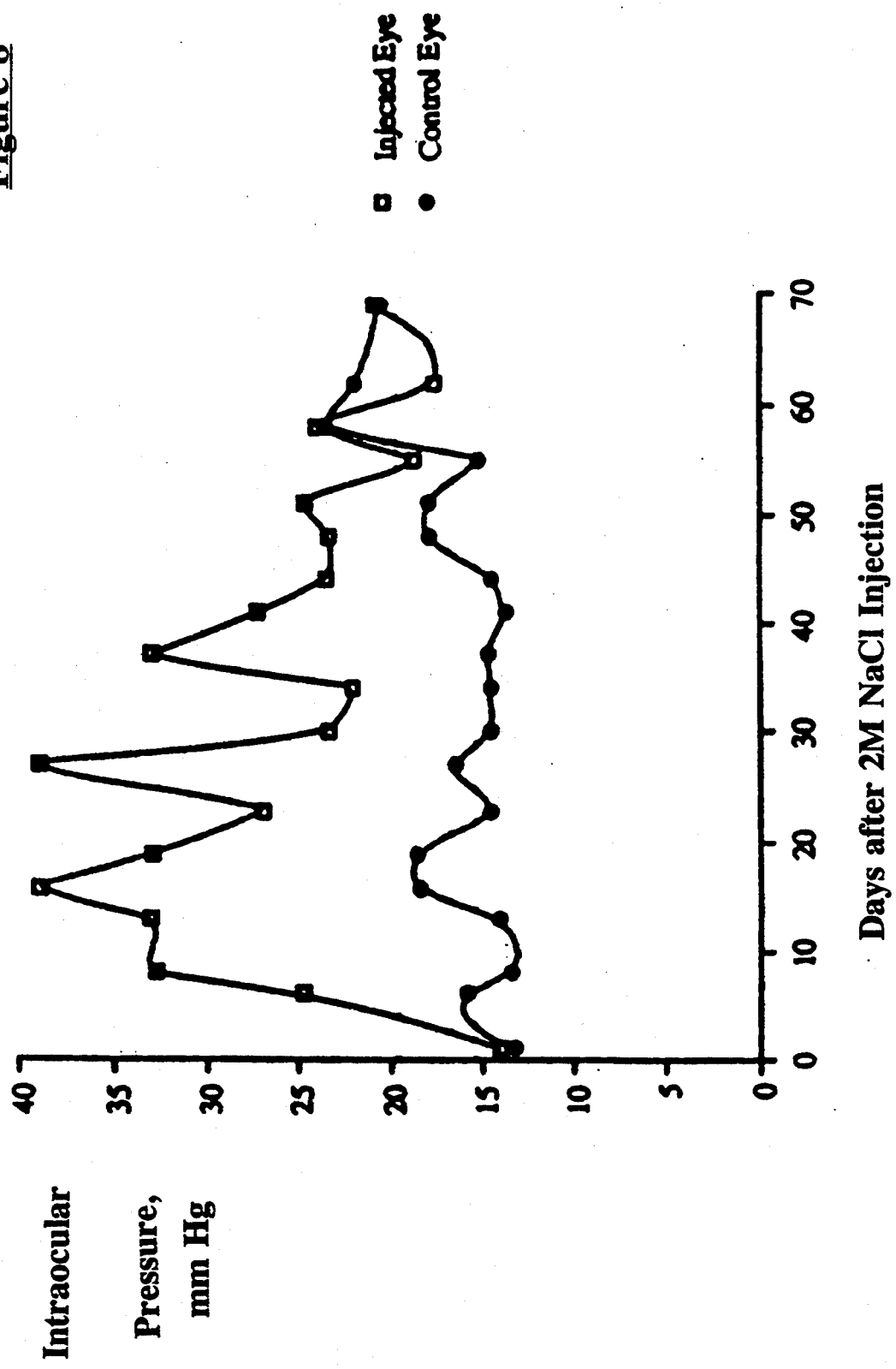
FIG. 8 presents the post-injection IOP response of one animal treated as described in Example 4.

18 injections of 2M saline on 12 rats have been performed to date. Of these injections, 11 resulted in IOP elevations of 10 to 30 mm Hg above normal. Eight of these 11 remained at elevated IOPs for up to 100 days, and one was sacrificed immediately after a significant elevation in IOP (15 mm Hg higher than fellow eye) was detected (6 days post-injection). FIG. 8 demonstrates a representative post-injection IOP response for one animal.

Eyes with pressure elevations of two weeks or more demonstrate mild, overall enlargement of the globe. The anterior chambers deepen and peripheral anterior synechiae occur. Histologic analysis confirms that the mechanism of acute pressure elevation is due to scarring of Schlemm's canal and the trabecular meshwork. Chronic angle closure has been seen several weeks after injection with sparing of the pigmented and non-pigmented ciliary epithelium.

Figure 9A:
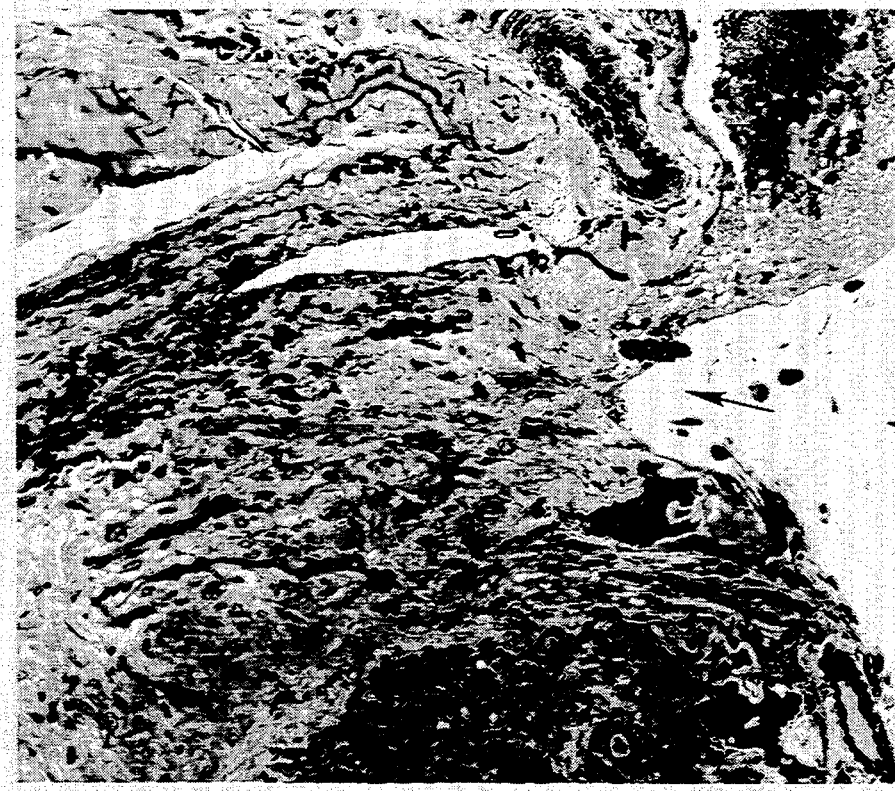
FIGS. 9A and 9B are a histological cross-section under low (Panel A) and high (Panel B) power microscopy showing cupping of the optic nerve head under conditions of chronically elevated intraocular pressure.
Figure 9B:
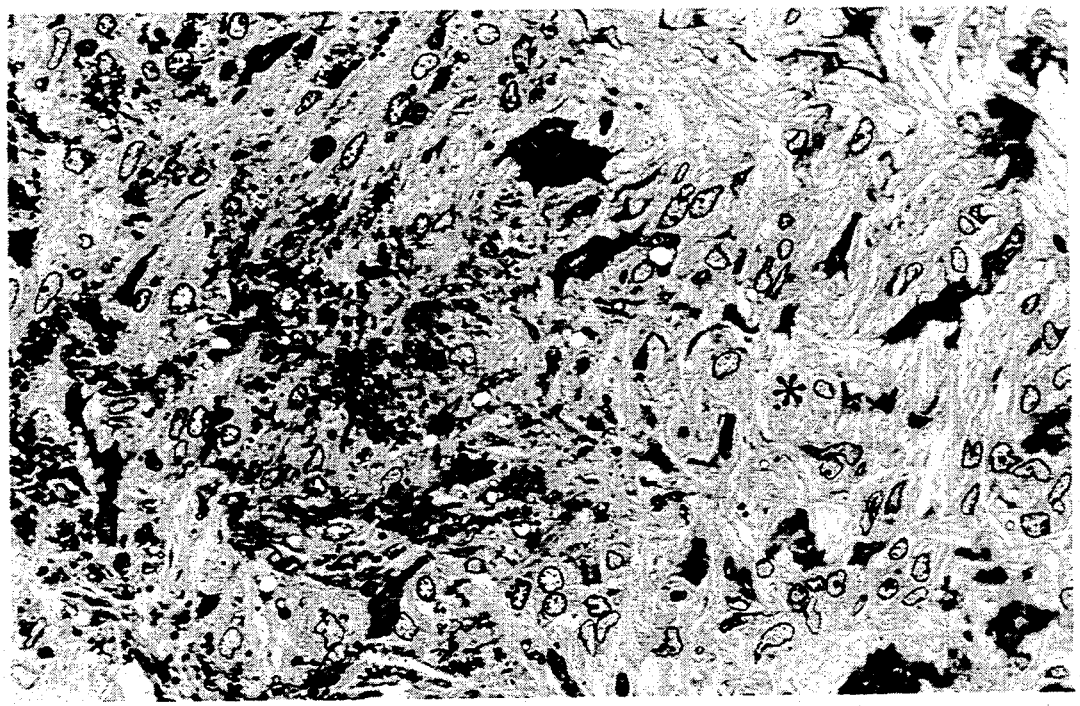

Eyes enucleated one week after pressure elevation demonstrate moderate disorganization of neuronal and glial elements with build up of cellular organelles and degenerating cellular debris at the level of the lamina cribrosa. Eyes with chronic pressure elevation show cupping (FIG. 9, arrow), disorganization and selective loss of retinal ganglion cells (asterisk, FIG. 10, compare Panel A with Panel B), and marked destruction of optic nerve fibers with myelin figures (arrow, FIG. 11, compare Panel A with Panel B). All of these histologic features are consistent with those seen in human glaucoma.

It should be understood that the foregoing disclosure emphasizes certain specific embodiments of the invention and that all modifications or alternatives equivalent thereto are within the spirit and scope of the invention as set forth in the appended claims.

What I claim is:

1. A method for evaluating changes in tissues in a mammalian eye associated with intraocular pressure, the method comprising:
    (a) administering a compound to one or both eyes of an animal wherein the compound produces an intraocular pressure modulating effect;
    (b) maintaining the intraocular pressure modulating effect of the compound for a time sufficient to produce tissue changes, whereby intraocular pressure is measured periodically with a non-invasive pressure detecting device; and
    (c) detecting the changes using the pressure-detecting device in tissues in a mammalian eye associated with the intraocular pressure modulating effect, wherein tissue damage is detected by immunohistochemical staining of ocular tissues.

2. The method of claim 1 wherein the tissues in the mammalian eye in which changes associated with the intraocular pressure modulating effect are detected are selected from the group consisting of the lamina cribosa, the optic nerve head, optic nerve axons, the retina, the aqueous trabecular meshwork of the iris, Schlemm's canal, the ocular vasculature and central nervous system projections of the optic nerve fibers.

3. A method for evaluating changes in tissues in a mammalian eye associated with intraocular pressure, the method comprising:
    (a) administering a compound to one or both eyes of an animal wherein the compound produces an intraocular pressure modulating effect;
    (b) maintaining the intraocular pressure modulating effect of the compound for a time sufficient to produce tissue changes, whereby intraocular pressure is measured periodically with a non-invasive pressure detecting device; and
    (c) detecting the changes using the pressure-detecting device in tissues in a mammalian eye associated with the intraocular pressure modulating effect, wherein tissue damage is detected by in situ hybridization of ocular tissues with at least one detectably-labeled, nucleic acid probe.

4. The method of claim 3 wherein the tissues in the mammalian eye in which changes associated with the intraocular pressure modulating effect are detected are selected from the group consisting of the lamina cribosa, the optic nerve head, optic nerve axons, the retina, the aqueous trabecular meshwork of the iris, Schlemm's canal, the ocular vasculature and central nervous system projections of the optic nerve fibers.

5. The method of claim 3 wherein the tissues in the mammalian eye in which changes associated with the intraocular pressure modulating effect are detected using a detectably-labeled nucleic acid probe that is detectably labeled with a radioactive, antigenic, hapten or fluorescent label.

6. The method of claim 3 wherein the tissues in the mammalian eye in which changes associated with the intraocular pressure modulating effect are detected using at least one detectably-labeled nucleic acid probes that is substantially homologous to a gene whose expression is induced in response to tissue damage.

7. The method of claim 6 wherein the tissues in the mammalian eye in which changes associated with the intraocular pressure modulating effect are detected using a nucleic acid probe that is substantially homologous to a nucleic acid selected from the group of nucleic acids encoding T-α-1-tubulin, peripherin, growth-associated protein (GAP)-43, axonin 1, synaptosomal-associated protein 25, brain-derived neurotrophic factor, laminin, vimentin, tenascin, and glial fibrillary acidic protein.

* * * * *